(12) United States Patent
Renken

(10) Patent No.: US 9,186,669 B2
(45) Date of Patent: Nov. 17, 2015

(54) FILTER DEVICE FOR FACILITATING CHARACTERIZING BEHAVIOR OF CELLS

(75) Inventor: Christian W. Renken, Niskayuna, NY (US)

(73) Assignee: APPLIED BIOPHYSICS, INC., Troy, NY (US)

( * ) Notice: Subject to any disclaimer, the term of this patent is extended or adjusted under 35 U.S.C. 154(b) by 612 days.

(21) Appl. No.: 13/370,460

(22) Filed: Feb. 10, 2012

(65) Prior Publication Data

US 2013/0210131 A1 Aug. 15, 2013

(51) Int. Cl.
| | | |
|---|---|---|
| B01L 3/00 | (2006.01) | |
| C12M 1/12 | (2006.01) | |
| C12M 1/42 | (2006.01) | |

(52) U.S. Cl.
CPC ............ *B01L 3/50255* (2013.01); *C12M 25/04* (2013.01); *C12M 35/02* (2013.01); *B01L 2300/0645* (2013.01); *B01L 2300/0681* (2013.01); *B01L 2300/0829* (2013.01); *Y10T 29/49002* (2015.01); *Y10T 29/494* (2015.01)

(58) Field of Classification Search
CPC ................ B01L 2300/0645; B01L 2300/0681; B01L 2300/0829; B01L 3/50255; C12M 25/04; C12M 35/02
USPC ............................................ 435/283.1–309.4
See application file for complete search history.

(56) References Cited

U.S. PATENT DOCUMENTS

| | | | |
|---|---|---|---|
| 6,140,045 A | 10/2000 | Wohlstadter et al. | |
| 7,332,313 B2 | 2/2008 | Giaever et al. | |
| 7,399,631 B2 | 7/2008 | Giaever et al. | |
| 2003/0215941 A1* | 11/2003 | Campbell et al. | ............. 435/325 |
| 2004/0043481 A1* | 3/2004 | Wilson | ....................... 435/297.1 |
| 2005/0153425 A1 | 7/2005 | Xu et al. | |
| 2005/0221282 A1 | 10/2005 | Owen et al. | |
| 2006/0051857 A1* | 3/2006 | Wedell et al. | ............. 435/289.1 |
| 2006/0105321 A1 | 5/2006 | Moy et al. | |
| 2007/0166816 A1* | 7/2007 | Campbell et al. | .......... 435/288.4 |
| 2008/0213855 A1 | 9/2008 | Firth et al. | |
| 2008/0251383 A1 | 10/2008 | Sobek et al. | |
| 2010/0190228 A1 | 7/2010 | Giaever et al. | |

OTHER PUBLICATIONS

Lo et al., "Rapid Communication—Cell-Substrate Contact: Another Factor May Influence Transepithelial Electrical Resistance of Cell Layers Cultured on Permeable Filters", Experimental Cell Research, No. 250, pp. 576-580 (1999).

* cited by examiner

*Primary Examiner* — Nathan Bowers
*Assistant Examiner* — Lydia Edwards
(74) *Attorney, Agent, or Firm* — Kevin P. Radigan, Esq.; Heslin Rothenberg Farley & Mesiti P.C.

(57) ABSTRACT

A filter device is provided which includes a well, at least one top access opening to the well, and a horizontally-disposed filter. The well, which includes an inner surface at least partially defining the well, also includes a first well chamber to accommodate a fluid and a second well chamber to accommodate a fluid. The first well chamber and the second well chamber are separate chambers, and the inner surface at least partially defines the first well chamber and at least partially defines the second well chamber. The at least one top access opening provides independent top access to the first well chamber and the second well chamber, and the horizontally-disposed filter is positioned between and at least partially separates the separate first well chamber and second well chamber of the well.

14 Claims, 5 Drawing Sheets

FILTER DEVICE FOR FACILITATING CHARACTERIZING BEHAVIOR OF CELLS

BACKGROUND

In many applications, filters are employed as substrates to facilitate animal cell growth. By way of example, cells may be grown on a filter support that is held, either vertically or horizontally, between two chambers. Once a cell monolayer is grown upon one side of the filter located between the two chambers, a variety of measurements can be made to characterize the cells, including, permeability of the cell layers, the ability of drugs to pass through the cell layer, the ability of cells to move through the filter, etc. These measurements may be made electrically, with the use of labeled compounds, such as dyes or radioisotopes, or simply by microscopically observing the cells.

One form of measuring cell behavior employs electrical sensing. One example of this is disclosed in U.S. Letters Pat. No. 5,187,096, which is hereby incorporated herein by reference, and referred to herein as the "ECIS® system". Specifically, the ECIS® system (Electric Cell-substrate Impedance Sensing), which is marketed by Applied BioPhysics, Inc., of Troy, N.Y., U.S.A., passively analyzes cell behavior by applying a weak AC current, and measuring voltage changes. The device can be used to monitor various cell behaviors, including morphology changes and cell motions in animal cells that are attached and spread out and crawl, for example, on the bottom of a tissue culture vessel. In the ECIS®system, cells are typically grown upon one or more small gold film electrodes (e.g., each $5 \times 10^{-4}$ to $10 \times 10^{-4}$ cm² in size), mounted to the bottom of a small well with (in one embodiment) a much larger counter-electrode completing the circuit using a standard tissue culture medium as an electrolyte. A weak (e.g., approximately 2 microamp) AC current (usually in the frequency range of 100 to 100,000 Hz) is applied to the electrode. This small current results in a voltage drop across the small, active electrode of only a few millivolts. Voltage drops this small do not affect the health of the cells.

Variations in the measured voltage comprise the measurement. As animal cells attach and spread upon the small, active electrode, they force the current to flow under and between the cells, resulting in changes in impedance, and hence, in the measured voltage across the electrodes. These changes can be followed and provide a non-invasive means to monitor changes in cell behavior. For example, using the measured voltages, one can infer cell morphology and cell movements, which are important research measurements that form the basis of many biomedical and biological assays.

Additionally, transepithelial resistance (TER) measurement has been used to study paracelluar transport properties of epithelia grown on permeable filters, especially the barrier function of tight junctions. The permeable filters are usually porated (track-etched pores), but can also be tortuous-path filters. Differences in making measurements in cell permeability with different types of filter supports is described by Lo et al. in a paper entitled, "Rapid Communication, Cell-Substrate Contact: Another Factor May Influence Transepithelial Electrical Resistance of Cell Layers Cultured on Permeable Filters", Experimental Cell Research 250, pages 576-580 (1999), which is hereby incorporated herein by reference in its entirety.

BRIEF SUMMARY

To assist with, for example, the above-described measurements, disclosed herein are enhanced filter device configurations which can be employed to more efficiently and economically facilitate characterizing, for instance, cells grown on a filter structure.

Provided herein, in one aspect, is an apparatus comprising at least one filter device. One filter device of the at least one filter device includes a well, at least one top access opening to the well, and a horizontally-disposed filter. The well is at least partially defined by an inner surface of the one filter device, and includes a first well chamber and a second well chamber. The first well chamber and the second well chamber are separate chambers, and the inner surface at least partially defines the first well chamber and at least partially defines the second well chamber. The at least one top access opening to the well provides independent top access to the first well chamber and to the second well chamber, and the filter is disposed horizontally within the well between and at least partially separating the separate first well chamber and second well chamber of the well.

In a further aspect, a method of fabricating a filter device is provided. The method includes: providing a well, the well comprising an inner surface at least partially defining the well, and at least partially defining a first well chamber and a second well chamber, the first well chamber and the second well chamber being separate chambers of the well, and the first well chamber to accommodate a first fluid and the second well chamber to accommodate a second fluid, the first fluid and the second fluid being a common fluid or different fluids; providing at least one top access opening to the well, the at least one top access opening allowing independent top access to the first well chamber and to the second well chamber; and disposing a filter horizontally within the well between and at least partially separating the separate first well chamber and second well chamber of the well.

Additional features and advantages are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Reference is made below to the drawings (which are not drawn to scale to facilitate an understanding of the invention), wherein the same reference numbers used throughout different figures designate the same or similar components.

Figure 1A:
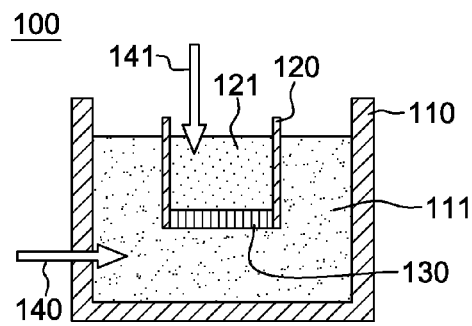
FIG. 1A depicts one embodiment of a conventional filter device comprising a filter well insert.

FIG. 1A depicts one embodiment of a conventional filter device 110 for characterizing, for example, cells introduced onto a filter 130 at the base of an inner well 120 (or filter well insert) suspended within an outer well 110. As shown, a first fluid 111 is disposed in outer well 110 and a second fluid 121 in inner well 120, and outer well 110 and inner well 120 are both open top wells. In operation, inner well 120 with filter 130 may be moved or dipped into the position illustrated in FIG. 1A, within first fluid 111 in outer well 110. If an electrical measurement is to be made across filter 130, then a first electrode 140 is provided at, for example, a side wall or base of outer well 110, and a dipping electrode 141 is inserted into second fluid 121 within inner well 120.

Although workable, a disadvantage of the filter device approach of FIG. 1A is that the inner well must be positioned within the outer well, and the dipping electrode must to be operatively positioned within the fluid in the inner well, both of which require processing steps and add to the time to perform one or more measurements for characterizing, for example, behavior of cells introduced onto the filter. Known variations on the filter device of FIG. 1A are generally more complex than the embodiment depicted, resulting in higher device costs and, depending upon the implementation, greater chances for components, such as spring-loaded pins, to become non-operative over time.

Figure 1B:
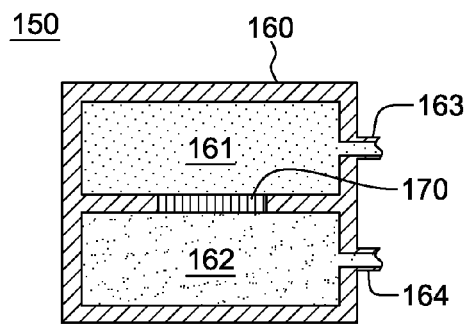
FIG. 1B depicts one embodiment of a conventional Ussing chamber-type filter device.

FIG. 1B depicts an alternate embodiment of a filter device 150, which is conventionally referred to as an Ussing chamber. In this embodiment, filter device 150 comprises a fluid-tight housing 160 with an upper chamber 161, shown with a first fluid, and a lower chamber 162, shown with a second fluid. The upper and lower chambers are separated by a filter 170, and the first and second fluids may be introduced into the upper and lower chambers 161, 162, respectively, via a sealable upper chamber port 163 and a sealable lower chamber port 164, both in a side wall of the fluid-tight housing 160. In one implementation, if electrical measurements are to be made to, for example, assist in characterizing behavior of cells on filter 170, electrodes must be inserted into the chambers through the upper chamber port 163 and lower chamber port 164, respectively.

A drawback to this measurement approach, and filter device, is that it does not lend itself well to high through-put characterization or analysis. For example, access to the upper and lower chambers is constrained by the sealable chamber ports being in the side wall of the fluid-tight housing, and additional processing time and steps are required to, for example, insert electrodes into the upper and lower chambers for performing one or more electrical characterizing measurements.

Generally stated, provided herein in one aspect, is an apparatus which comprises at least one filter device, or an array of filter devices. The filter device includes a well that comprises an inner surface that at least partially defines the well. The well further includes a first well chamber to accommodate a first fluid (or solution), and a second well chamber to accommodate a second fluid (or solution), wherein the first and second fluids may be the same type of fluid, or different types of fluids. The first well chamber and the second well chamber are separate well chambers within the well, and the inner surface at least partially defines the first well chamber and at least partially defines the second well chamber, that is, the inner surface is a common well surface to both the first well chamber and the second well chamber. In one example, the common well surface is a common planar well surface.

One or more top access openings are provided for the well, which allows independent top access to the first well chamber and the second well chamber. A filter is disposed within the well horizontally between and at least partially separating the separate first well chamber and second well chamber of the well.

Advantageously, the at least one top access opening provides convenient top access to both the first well chamber and the second well chamber, notwithstanding the horizontal disposition of the filter between the first and second well chambers of the well. By positioning the filter horizontally, inoculation of the filter with cells using standard tissue culture techniques is facilitated. Further, by configuring an inner surface of the well to be common to both the first well chamber and the second well chamber, it is convenient to introduce two or more sensors at the common inner surface, with each sensor being associated with a respective well chamber of the first and second well chambers. In one embodiment, the common inner surface comprises a base or a side wall of the well. Note, in this regard, that a common inner base surface refers to the base surface of the first well chamber and the base surface of the second well chamber, and that these base surfaces need not necessarily be coplanar, but rather, may reside in parallel planes. Similarly, the common inner side wall surface comprises a common side wall surface of the first well chamber and the second well chamber, but these common inner side wall surfaces need not necessarily be coplanar, but rather, may alternatively (for example) reside in parallel planes.

In an enhanced implementation, the two or more sensors may comprise a first electrode and a second electrode disposed, for example, coplanar at a planar, common inner surface of the well of the filter device. These first and second electrodes, which may be located, for example, on the base surface of the well, facilitate measuring conductivity of the filter, or more commonly, conductivity of the filter covered with cells or gels of molecular layers. The first and second electrodes are each associated with a respective one of the first and second well chambers, and electrical connection through the medium on the upper side of the horizontally-disposed filter is provided via the first and second fluids (or solutions) within the chambers. Note that various configurations of the filter device are possible employing the concepts disclosed herein.

Advantageously, the filter device disclosed herein can be employed for a number of cell electrophysiological measurements. For example, the filter device with electrodes could be used for TER measurements, including trans-epithelial or trans-endothelial cell measurements, where cells are grown upon the filter and the permeability of the cell layer is measured electrically. The filter device with electrodes could also be used to perform cell migration measurements through a porated (e.g., track etched) filter. Sensors, other than electrodes, could alternatively be employed to facilitate further types of measurements. For example, densitometers, or optical or chemical sensors or detectors could be located at, or in association with, the common inner surface of the well disclosed herein. Additionally, the filter devices disclosed herein could be employed to measure transport of material through the filter and, for instance, across cultured cell monolayers or tissue samples. Various methods of fabrication and device configurations are presented. As a further example, FIGS. 5A-5D depict one embodiment of an apparatus which comprises an array of filter devices, configured as described herein. This apparatus could comprise any number of filter devices and be fabricated, by way of example, by laminating layers of material with specified openings onto a substrate comprising a printed circuit board having the desired sensors (or electrodes), as explained below.

Figure 2A:
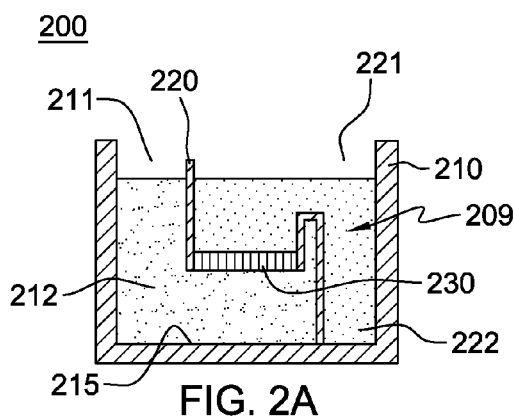
FIG. 2A depicts one embodiment of a filter device, in accordance with one or more aspects of the present invention.

FIG. 2A depicts one embodiment of a filter device 200, in accordance with one or more aspects of the present invention. As shown, filter device 200 includes a well 209 within a fluid-tight container 210 (or structure). Separate well chambers are defined, in this embodiment, by an inner dividing wall 220 within fluid-tight container 210. Specifically, a first well chamber 212 and a second well chamber 222 are provided, separated by inner dividing wall 220, as well as by a horizontally-disposed filter 230 positioned within the well in an opening in the inner dividing well. Well chambers 212, 222 may comprise the same fluid (or solution), or different fluids (or solutions), depending on the application. As illustrated in FIG. 2A, well 209 further includes at least one top access opening to the first and second chambers 212, 222. In this embodiment, a first top access opening 211 is provided to first well chamber 212, and a second top access opening 221 is provided to second well chamber 222. Additionally, the filter device 200 is configured with a common inner base surface 215, which partially defines both the first well chamber 212 and the second well chamber 222. Advantageously, as depicted in FIG. 2B, this facilitates provision of coplanar sensors (or, in one embodiment, electrodes) in association with the first and second well chambers, and thus facilitates fabrication of the filter device.

Figure 2B:
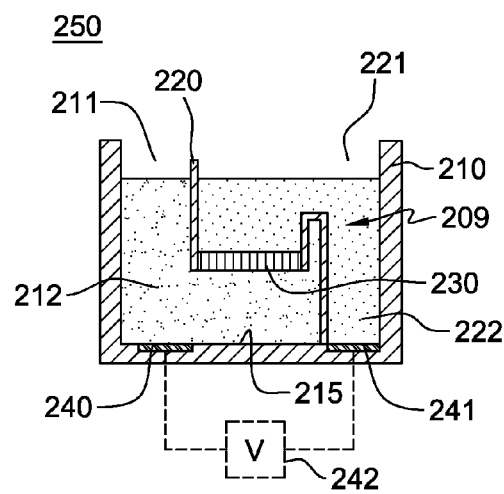
FIG. 2B depicts an enhanced embodiment of the filter device of FIG. 2A, shown with coplanar first and second sensors (for example, electrodes) at an inner base surface of the filter device, which facilitate characterizing cells introduced into the filter, in accordance with one or more aspects of the present invention.

FIG. 2B depicts an alternate embodiment of a filter device, generally denoted 250, in accordance with one or more aspects of the present invention. Filter device 250 is substantially identical to filter device 200 described above in connection with FIG. 2A, except that, as illustrated in FIG. 2B, one or more first sensors 240 are disposed in association with first well chamber 212 at or parallel to the common inner surface 215 of well 209, and one or more second sensors 241 are disposed in association with the second well chamber 222 at or parallel to the common inner surface 215 of the well 209. In this embodiment, the common inner surface 215 is a planar base surface of the well. Advantageously, by providing a planar inner surface which at least partially defines both the first well chamber and the second well chamber, two or more sensors 240, 241 may be conveniently placed coplanar during device fabrication so as to be integrated with the filter device, thus eliminating the need for moving parts in order to perform a desired measurement, such as the case with the device embodiments of FIGS. 1A & 1B. In the example of FIG. 2B, sensors 240, 241 may, in one example, comprise a first electrode and second electrode, respectively, and be electrically connected to a circuit comprising a controllable electrical signal source 242. In operation, when electrical signal source 242 applies a signal across the electrodes, the first and second electrodes direct an electrical field between them through the fluid(s) or solution(s) in the first and second well chambers 212, 222, and across the horizontally-disposed filter 230, and any cells (not shown) disposed on the filter, in order to, for example, characterize behavior of the cells.

Figure 3A:
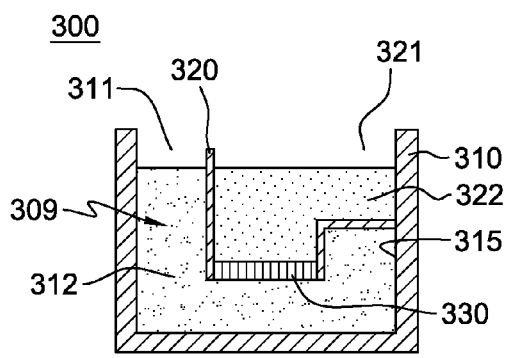
FIG. 3A depicts an alternate embodiment of a filter device, in accordance with one or more aspects of the present invention.

FIG. 3A depicts an alternate embodiment of a filter device 300, in accordance with one or more aspects of the present invention. In this embodiment, filter device 300 includes a well 309 within a fluid-tight container 310 (or structure). Separate first and second well chambers 312, 322 are defined, via an inner dividing wall 320 within well 309 of fluid-tight container 310. Additionally, the first and second well chambers 312, 322 are separated by a horizontally-disposed filter 330 positioned within the well in an opening in the inner dividing wall 320. Well chambers 312, 322 may comprise the same fluid (or solution), or different fluids (or solutions), depending upon the application. As illustrated in FIG. 3A, well 309 further includes at least one top access opening to the first and second chambers 312, 322. In this example, well 309 is an open top well, which can be characterized as including a first access opening 311 to first well chamber 312, and a second top access opening 321 to second well chamber 322. Additionally, filter device 300 comprises a common inner side wall surface 315, which partially defines both the first well chamber 312 and the second well chamber 322, as illustrated. As noted above, this advantageously facilitates provision of sensors (or electrodes) in associated with a surface that at least partially defines the first and second well chambers, and thus, facilitates fabrication of the filter device.

Figure 3B:
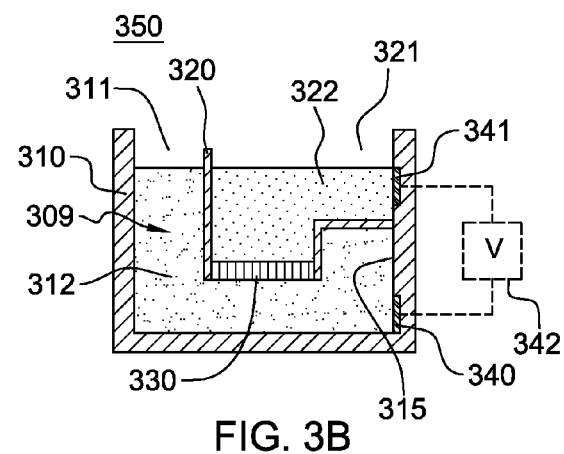
FIG. 3B depicts an enhanced embodiment of the filter device of FIG. 3A, shown with coplanar first and second sensors (for example, electrodes) at an inner side wall surface of the filter device, which facilitate characterizing cells introduced onto the filter, in accordance with one or more aspects of the present invention.

FIG. 3B depicts an enhanced embodiment of filter device 300 of FIG. 3A. In this embodiment, a filter device 350 is presented which is substantially identical to filter device 300 of FIG. 3A, but with the provision of one or more sensors 340, 341 in association with each of the separate well compartments 312, 322. In the example of FIG. 3B, one or more first sensors 340 are disposed in association with first well chamber 312 at or parallel to the common inner side wall surface 315 of well 309, and one or more second sensors 341 are disposed in association with the second well chamber 322 at or parallel to the common inner side wall surface 315 of well 309. In this embodiment, the common inner side wall surface 315 is a side wall surface of well 309. As noted, by providing a common inner surface that partially defines both the first well chamber and the second well chamber, two or more sensors 340, 341 may be conveniently placed during device fabrication so as to be integrated with the filter device, and not require any moving parts in order to perform (for example) one or more of a fluid, filter and/or cell characterizing measurement.

In an enhanced embodiment, sensors 340, 341 comprise a first electrode and a second electrode interconnected through a circuit that includes a controllable electrical signal source 342. In operation, the electrical signal source 342 applies a signal across the electrodes, and the first and second electrodes facilitate directing an electrical field through the fluid(s) or solution(s) in the first and second well chambers 312, 322, and across the horizontally-disposed filter 330, and any cells (not shown) disposed on the filter, for example, in order to characterize behavior of the cells.

Figure 4:
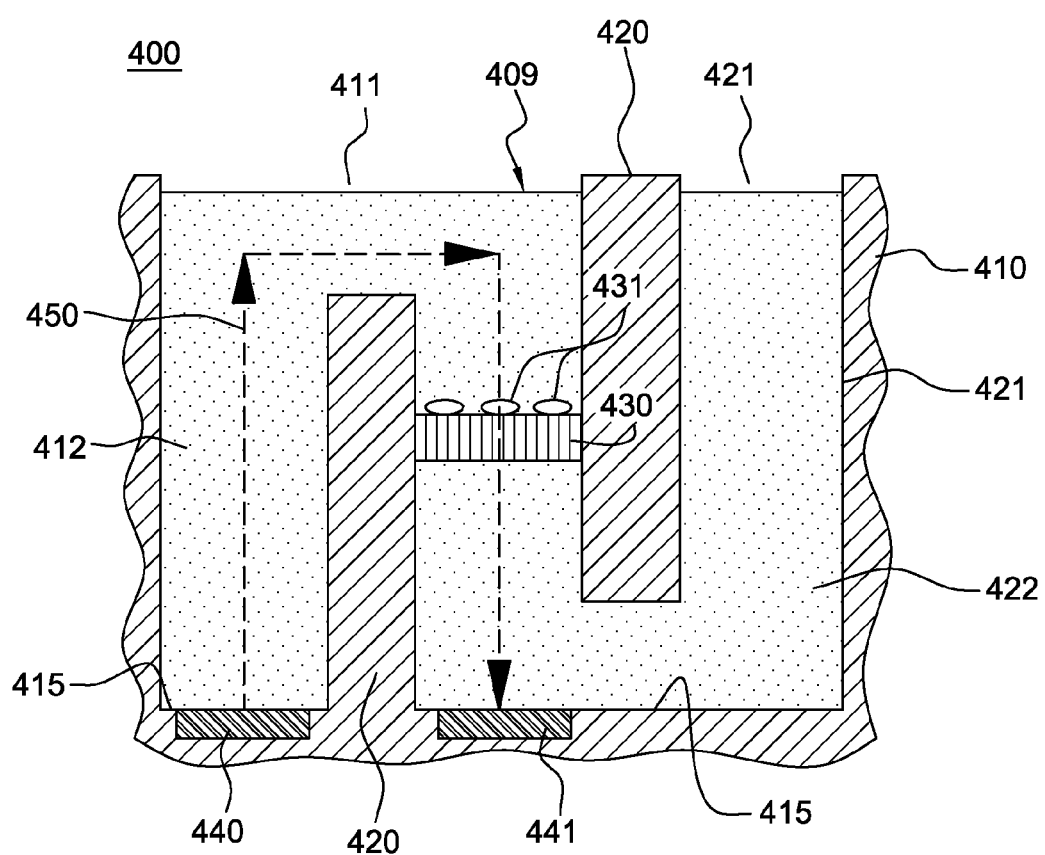
FIG. 4 depicts another embodiment of a filter device, in accordance with one or more aspects of the present invention.

FIG. 4 depicts a further embodiment of a filter device 400, in accordance with one or more aspects of the present invention. In this embodiment, filter device 400 includes a well 409 within a fluid-tight container 410 (or structure). Fluid-tight container 410 includes inner dividing walls 420 which facilitate defining separate well chambers, including a first well chamber 412 and a second well chamber 422. In addition to being separated by inner dividing walls 420, the first and second well chambers 412, 422 are separated by a horizontally-disposed filter 430, which in the illustrated embodiment, has been inoculated with cells 431 on an upper surface of the filter. By way of example, filter 430 could reside on a filter support (not shown) defined by or between inner dividing walls 420. Fluid-tight container 410 further includes at least one top access opening, which in this embodiment, includes a first top access opening 411 to first well chamber 412, and a second top access opening 421 to second well chamber 422. Additionally, in this example, well 409 is configured with a base surface 415, which partially defines both the first well chamber 412 and the second well chamber 422.

In the embodiment of FIG. 4, filter device 400 includes a first sensor 440 and a second sensor 441 respectively associated with the first well chamber 412 and second well chamber 422 of the filter device. By way of example, the first and second sensors 440, 441 are disposed at or parallel to the base surface 415 of the filter device. As noted above, in one implementation, sensors 440, 441 may comprise respective electrodes which allow for the application of an electromagnetic field or current flow 426 extending through fluids in first well chamber 412 and second well chamber 422, across horizontally-disposed filter 430 and the cells 431 disposed on the upper surface thereof to, for example, characterize behavior of the cells. This filter device could be employed in combination with measurements of the above-referenced ECIS® system, marketed by Applied BioPhysics, Inc.

Characterized otherwise, filter device 400 illustrated in FIG. 4 is a relatively small manifold device which conceptually includes at least three vertical channels. A central channel contains the horizontally-disposed filter 430 and is connected in fluid communication above the filter to one auxiliary channel on one side of the filter, forming first well chamber 412, and is connected in fluid communication below the filter to another auxiliary channel on an opposite side of the filter, forming second well chamber 422. As with the embodiments of FIGS. 2A-3B, the design of FIG. 4 allows for sensors to be placed at a common inner surface of the defined well, that is, at the base of the well, in this example. As a specific application, coplanar electrodes may be placed at the base of the well, with each electrode being associated with a respective well chamber on the different sides of the horizontally-disposed filter. This configuration advantageously allows for, for example, electrical impedance measurements across the filter. The basic design of FIG. 4 can be repeated to create multiple independent channels for, for example, facilitating multiple TER measurements.

Note further that filter device 400 of FIG. 4 also advantageously allows for the ability to add fluid from respective top access openings to the first and second well chambers independently. In addition, the filter device design of FIG. 4 can be implemented by numerous types of channel geometries. For example, the three-vertical-channel configuration of FIG. 4 could alternatively be arranged as a triangle, rather than be linearly arranged (as illustrated). Additional channels or sensors/electrodes can be added for additional geometries and/or measurements, if desired. Note again that many types of sensors other than electrodes could be employed in combination with the filter device. By way of example, optical sensors could be employed offset, if desired, from the main filter channel directly below the horizontally-disposed filter. Such a configuration would allow for the passage of fluorescent probes across the filter membrane to be measured without interference from a signal from above the horizontally-disposed filter. This can be accomplished with or without the presence of electrical electrodes. Note that in all embodiments discussed herein, more than one sensor or electrode of the same or different types or configurations could be employed in association with each well chamber of the filter device.

In one application, the filter devices disclosed herein provide a platform upon which to characterize the behavior of cells when introduced onto the filter. As noted above, one metric by which the cells may be characterized is how they alter an AC current between two electrodes provided in association with the filter device. A secondary metric would be the use of optical measures to monitor the passage of molecules through the horizontally-disposed filter (or membrane), and the resulting effects due to the presence of cells upon the filter. The inclusion of multiple electrodes in the first well chamber and multiple electrodes in the second well chamber (and/or one or more sensors in the first well chamber and one or more sensors in the second well chamber) may also be employed, depending upon the application, and the desired characterization measurements.

Note further that, with the filter device designs of FIGS. 2A-4, cells may be introduced onto an upper surface of the filter through a top access opening aligned over the top of the filter. Additionally, if desired, cells could be introduced onto the bottom surface of the filter, or onto both the top and bottom surfaces. The cells used need not be homogeneous, and the filter device disclosed herein could be employed to create complex systems of cells.

FIGS. 5A-5D depict one embodiment of an apparatus, generally denoted 500, comprising an array of filter devices 501, in accordance with one or more aspects of the present invention.

Referring collectively to FIGS. 5A-5D, apparatus 500 includes, in this example, a printed circuit board or substrate 510, and multiple layers 512, 514, 516 & 518, which are configured with openings that align to define the array of filter devices. Each filter device 501 comprises a well with separate first and second well chambers 520, 521 separated, at least partially, by a horizontally-disposed filter 530. In the embodiment illustrated, each filter device 501 also includes a first sensor (or electrode) 540 associated with first well chamber 520, and a second sensor (or electrode) 541 associated with second well chamber 521.

Figure 5A:
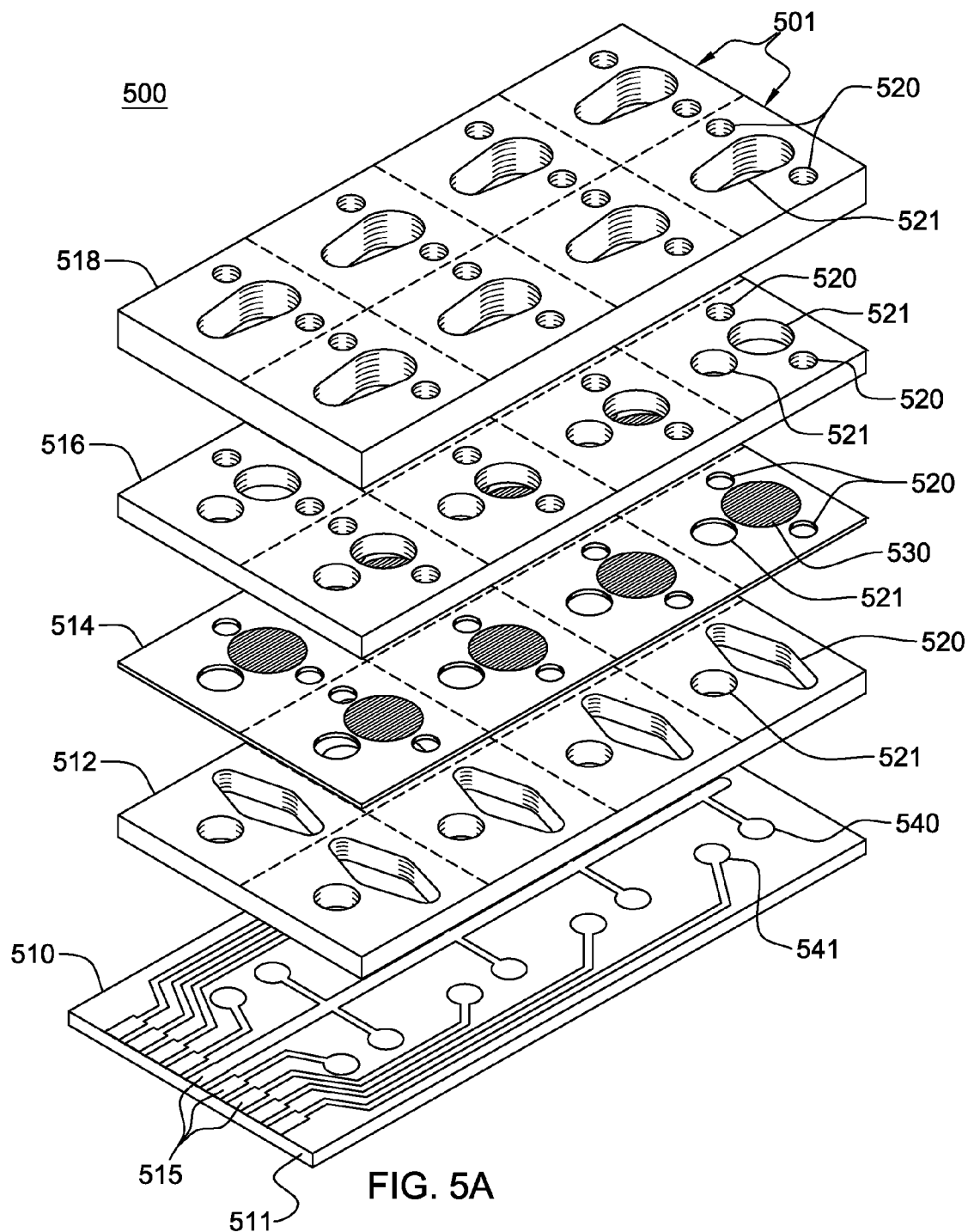
FIG. 5A is a partially exploded view of one embodiment of an apparatus comprising an array of filter devices, in accordance with one or more aspects of the present invention.
Figure 5B:
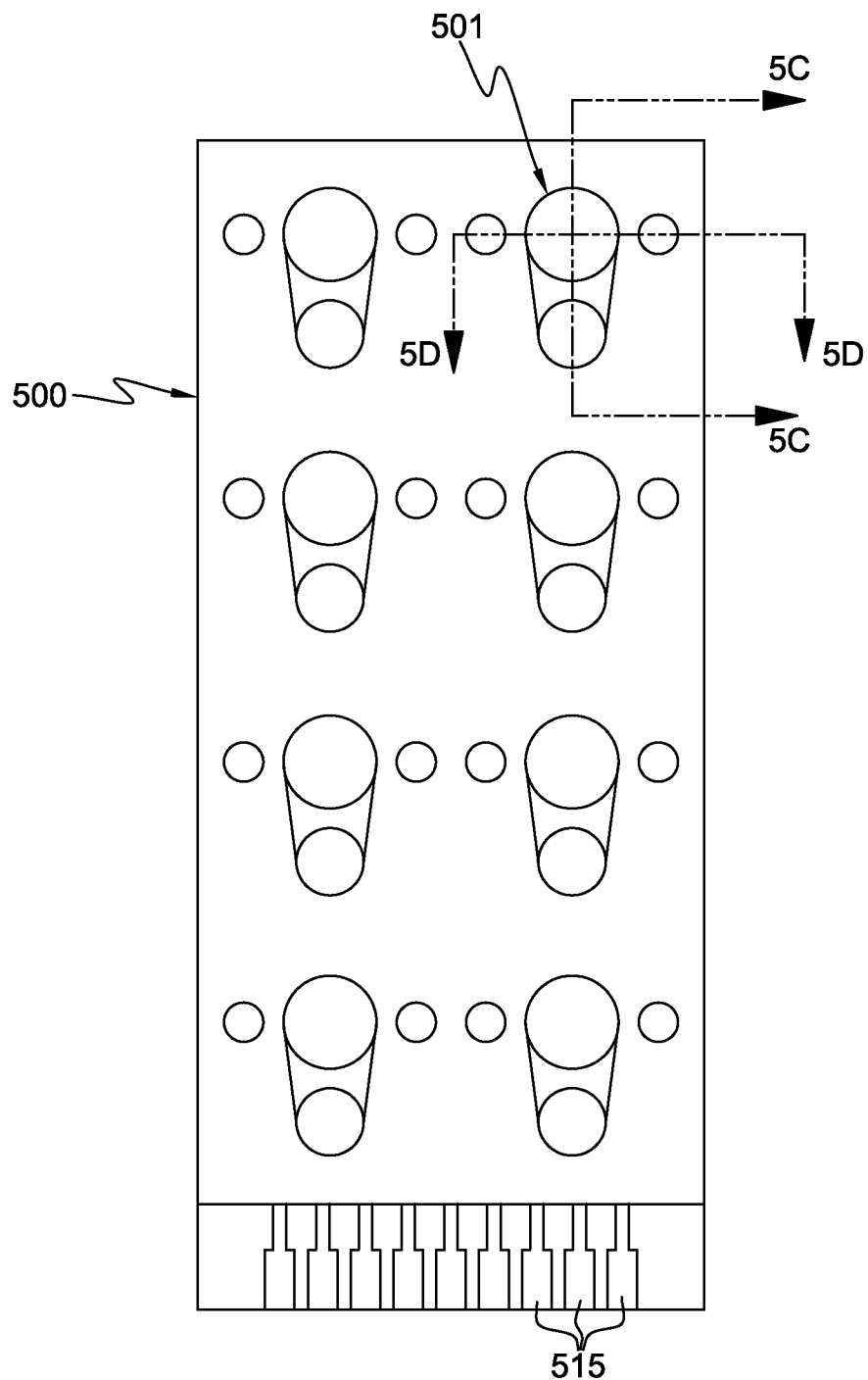
FIG. 5B is a top plan view of the apparatus of FIG. 5A, in accordance with one or more aspects of the present invention.
Figure 5C:
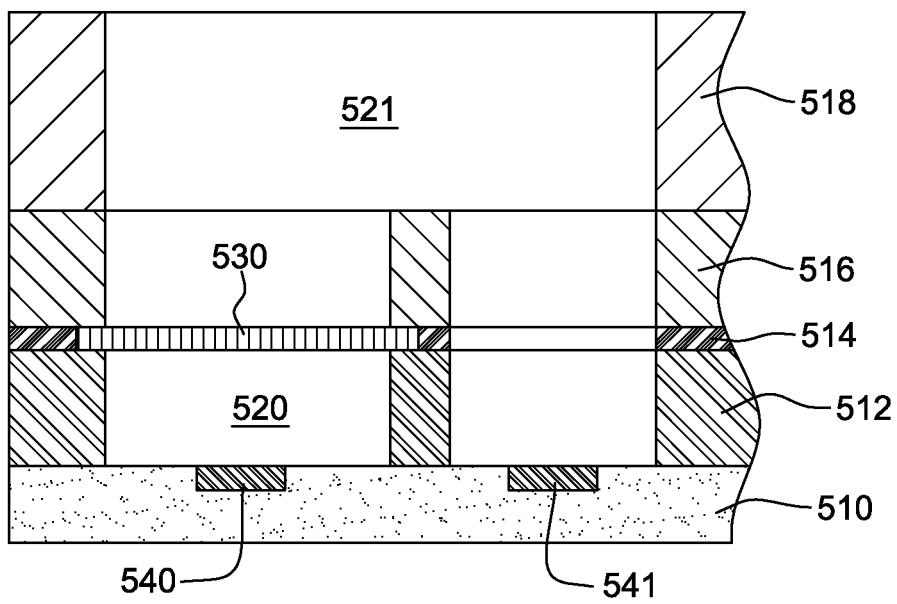
FIG. 5C is a partial cross-sectional elevational view of the apparatus of FIGS. 5A & 5B, taken along line 5C-5C in FIG. 5B, in accordance with one or more aspects of the present invention.
Figure 5D:
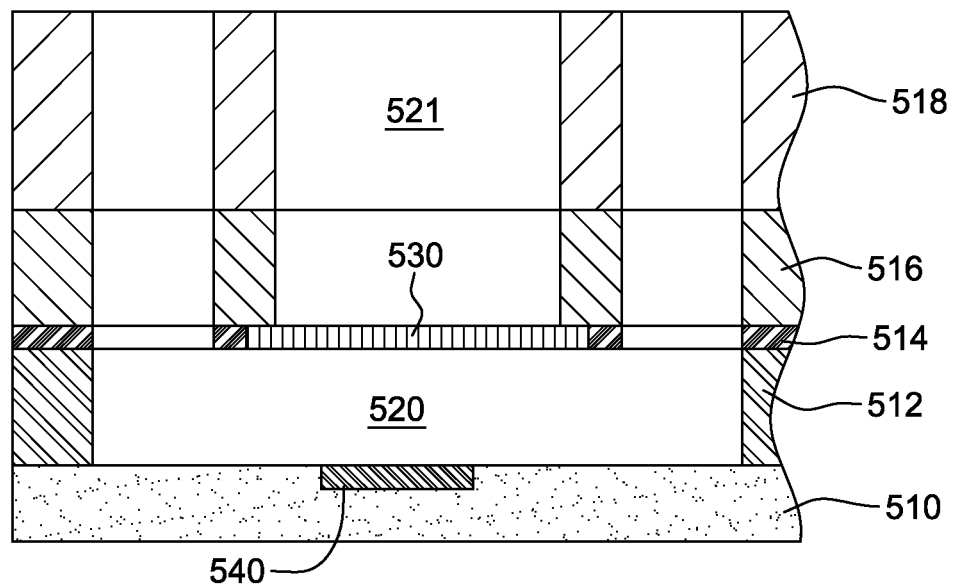
FIG. 5D is a partial cross-sectional elevational view of the apparatus of FIGS. 5A & 5B, taken along line 5D-5D in FIG. 5B, in accordance with one or more aspects of the present invention.

As depicted in FIGS. 5C & 5D, first well chamber 520 extends at least partially below horizontally-disposed filter 530, and second well chamber 521 extends at least partially over horizontally-disposed filter 530. Advantageously, printed circuit board or substrate 510 includes signal lines from the respective sensors (or electrodes) out to a common edge 511, which allows for aligned interconnects 515 to be exposed at the edge, and for the apparatus to be readily connected to a testing system (not shown) for automated testing of, for example, cells disposed on the upper surface of the horizontally-disposed filters in the respective filter devices 501 of the apparatus. Advantageously, the sensors or electrodes (in one example) for the filter devices 501 in the array of filter devices are fabricated on a common printed circuit board (or substrate), with the balance of the filter devices being defined by one or more structures or layers coupled to the printed circuit board (or substrate). This advantageously allows for the sensors to be integrated into the fabrication process, and eliminates the need for electrodes to be manually or automatically inserted into one or more of the compartments (chambers) of the filter device during the measurement process, as is the case with the initially-described prior art filter devices.

Manufacture of apparatus 500 can be accomplished in a number of ways. For example, the apparatus could be formed by milling layers of plastic or other insulating material and then laminating the layers into a single apparatus using adhesive(s), and the filters could be introduced into the laminated structure between the layers of the apparatus. Alternatively, layers of plastic could be secured together via clamps, with gaskets between the plastic sheets that provide a fluid-tight seal. In both cases, the horizontally-disposed filters are introduced into the respective filter devices by suspending them between, for example, two layers of the apparatus. In an alternate implementation, the apparatus could be fabricated of less layers, or even a single layer. In a single piece design, the apparatus could be made via injection molding. The filter would then be introduced into the filter device from one side. In all cases, the substrate (or printed circuit board containing the electrodes or sensors) could be made separate from the structures defining the well(s), and could be mounted to an assembled surface of the structures. This could be accomplished via adhesive for a permanent assembly, or via clamps and gaskets for easy disassembly, for example, for partial reuse of the apparatus.

In the embodiment of FIGS. 5A-5D, multiple filter devices per apparatus are assumed. Note that, although shown as an eight-filter device configuration, there is no restriction on the placement or number of filter devices that could be integrated into a single apparatus.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

What is claimed is:

1. An apparatus comprising:
   at least one filter device, one filter device of the at least one filter device comprising:
   a well, the well being at least partially defined by an inner base surface of the one filter device;
   the well further comprising an inner dividing wall extending from the inner base surface and dividing the well into a first well chamber and a second well chamber, the first well chamber and the second well chamber being separate chambers of the one filter device, and a first portion of the inner base surface of the one filter device at least partially defining the first well chamber and a second portion of the inner base surface of the one filter device at least partially defining the second well chamber;
   at least one top access opening to the well, the at last one top access opening allowing independent top access to the first well chamber and the second well chamber; and
   a horizontally-disposed filter positioned within the well and supported, at least in part, by the inner dividing wall, the horizontally-disposed filter being disposed between and facilitating separating the separate first well chamber and second well chamber.

2. The apparatus of claim 1, wherein the one filter device further comprises a first electrode and a second electrode, at least one of the first electrode or the second electrode being disposed at the inner base surface of the well of the one filter device, the first electrode being associated with the first well chamber and the second electrode being associated with the second well chamber, and the first electrode and the second electrode facilitating directing an electrical field therebetween through fluid in the first well chamber and the second well chamber and across the horizontally-disposed filter between the first well chamber and the second well chamber.

3. The apparatus of claim 2, wherein the first electrode and the second electrode are both disposed at the inner base surface of the well of the one filter device, and are coplanar.

4. The apparatus of claim 1, further comprising a first sensor and a second sensor, the first sensor being associated with the first well chamber and the second sensor being associated with the second well chamber.

5. The apparatus of claim 4, wherein the horizontally-disposed filter supports cells introduced onto the filter, and the first sensor and the second sensor facilitate characterizing behavior of the cells introduced onto the filter.

6. The apparatus of claim 4, wherein the first sensor and the second sensor are both disposed substantially parallel to the inner base surface of the one filter device.

7. The apparatus of claim 6, wherein the inner base surface is fabricated of a transparent material.

8. The apparatus of claim 1, wherein the horizontally-disposed filter supports cells introduced onto the filter, and the at least one top access opening comprises an opening positioned to facilitate top access viewing of the cells introduced onto the horizontally-disposed filter.

9. The apparatus of claim 1, wherein the horizontally-disposed filter comprises one of a porated filter or a tortuous-path filter.

10. The apparatus of claim 1, wherein the well is an open well with open top access to the well through the at least one top access opening, and wherein the one filter device further comprises a first electrode and a second electrode disposed at the inner base surface of the one filter device or a first sensor and a second sensor disposed at the inner base surface of the one filter device.

11. An apparatus comprising:
    at least one filter, device, one filter device of the at least one filter device comprising:

a well, the well being defined an inner surface of the one filter device;

the well further comprising a first well chamber and a second well chamber, the first well chamber and the second well chamber being separate chambers of the one filter device, and the inner surface at least partially defining the first well chamber and at least partially defining the second well chamber;

at least one top access opening to the well, the at last one top access opening allowing independent top access to the first well chamber and the second well chamber;

a horizontally-disposed filter positioned within the well between and at least partially separating, the separate first well chamber and second well chamber;

wherein the inner surface comprises an inner side wall surface of the well of the at least one filter device; and a first electrode and a second electrode, at least one of the first electrode or the second electrode being disposed at the inner side wall surface of the well of the one filter device, the first electrode being associated with the first well chamber and the second electrode being associated with the second well chamber, and the first electrode and the second electrode facilitating directing an electrical field therebetween through fluid in the first well chamber and the second well chamber and across the horizontally-disposed filter between the first well chamber and the second well chamber.

12. The apparatus of claim 11, wherein the first electrode and the second electrode are both disposed at the inner side wall surface of the well of the one filter device, and are coplanar.

13. An apparatus comprising:

at least one filter device, one filter device of the at least one filter device comprising:

a well, the well being at least partially defined by an inner surface of the one filter device;

the well further first well chamber and a second well chamber, the first well chamber and the second well chamber being separate chambers of the one filter device, and the inner surface at least partially defining the first well chamber and at least partially defining the second well chamber;

at least one top access opening to the well, the at last one top access opening allowing independent top access to the first well chamber and the second well chamber;

a horizontally-disposed filter positioned within the well between and at least partially separating the separate first well chamber and second well chamber; and wherein the apparatus further comprises an array of filter devices disposed on a printed circuit board, the printed circuit board comprising multiple electrodes, a first electrode and a second electrode of the multiple electrodes are associated with the one filter device, and wherein the first electrode and the second electrode are disposed at the inner base surface of the one filter device, and the first electrode is associated with the first well chamber and the second electrode is associated with the second well chamber, the first electrode and the second electrode facilitating directing an electrical field therebetween through fluid in the first well chamber and the second well chamber and across the horizontally-disposed filter between the first well chamber and the second well chamber, and wherein the first electrode and the second electrode of the printed circuit board are coplanar.

14. The apparatus of claim 1, wherein the one filter device comprises multiple top access openings, one top access opening of the multiple top access openings providing top access to the first well chamber, and two other top access openings of the multiple top access openings providing top access to the second well chamber, wherein the first well chamber extends above the horizontally-disposed filter, and the second well chamber extends below the horizontally-disposed filter.

\* \* \* \* \*